United States Patent [19]
Shan

[11] Patent Number: 5,984,860
[45] Date of Patent: Nov. 16, 1999

[54] PASS-THROUGH DUODENAL ENTEROSCOPIC DEVICE

[76] Inventor: Yansong Shan, 42149 Hartford, Canton, Mich. 48187

[21] Appl. No.: 09/047,563

[22] Filed: Mar. 25, 1998

[51] Int. Cl.⁶ ........................................................ A61B 1/05
[52] U.S. Cl. .......................... 600/116; 600/110; 600/132; 600/179
[58] Field of Search ..................................... 600/101, 104, 600/106, 109, 110, 114, 115, 116, 117, 118, 128, 129, 132; 604/96

[56] References Cited

U.S. PATENT DOCUMENTS

| | | | |
|---|---|---|---|
| 4,217,045 | 8/1980 | Ziskind | 600/116 X |
| 4,708,434 | 11/1987 | Tsuno | 600/116 X |
| 4,737,142 | 4/1988 | Heckele | 600/116 X |
| 5,364,353 | 11/1994 | Corfitsen et al. | 600/116 X |
| 5,454,364 | 10/1995 | Kruger | 600/114 |

Primary Examiner—John P. Leubecker
Attorney, Agent, or Firm—James M. Deimen

[57] ABSTRACT

A pass-through duodenal enteroscopic device utilizes the natural contraction wave of the small intestine to propel the device through the small intestine at about the same speed as any other object therein. The exterior of the device is streamlined over the greater portion thereof with a video camera and illumination source at the forward end of the device. Covering the camera lens and illumination source is a transparent inflatable balloon adapted to gently expand the small intestine immediately forward the camera for better viewing. A small diameter communication and power cable is wound within the device and unwinds through an aperture in the rear of the device as the device moves through the small intestine. Upon completion of movement through the small intestine the cable is automatically separated from the device permitting the cable to be withdrawn through the stomach and intestine. The device continues through the large intestine and passes from the patient through the rectum.

21 Claims, 10 Drawing Sheets

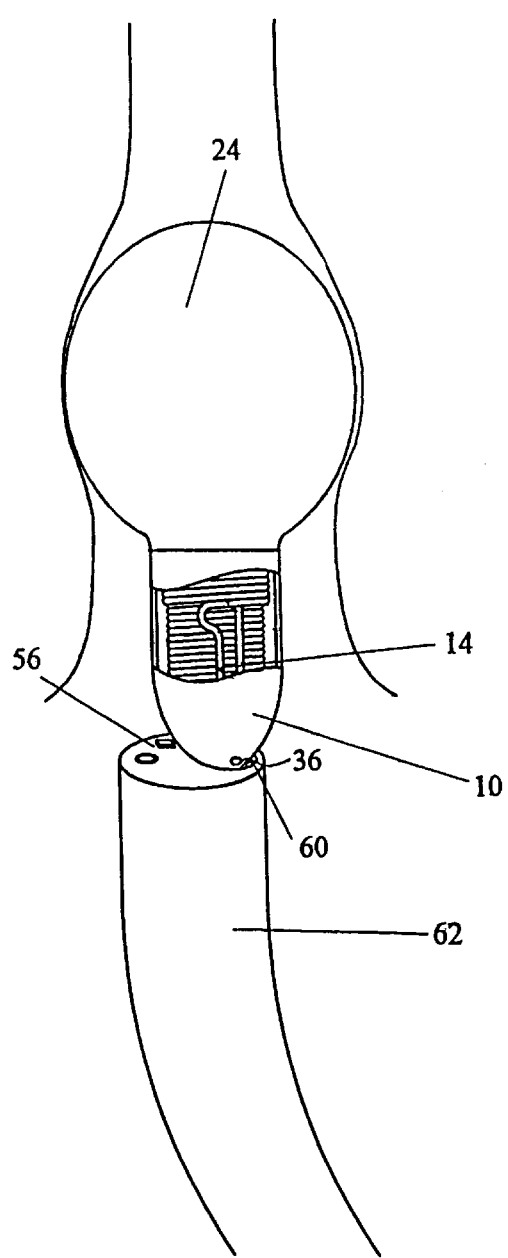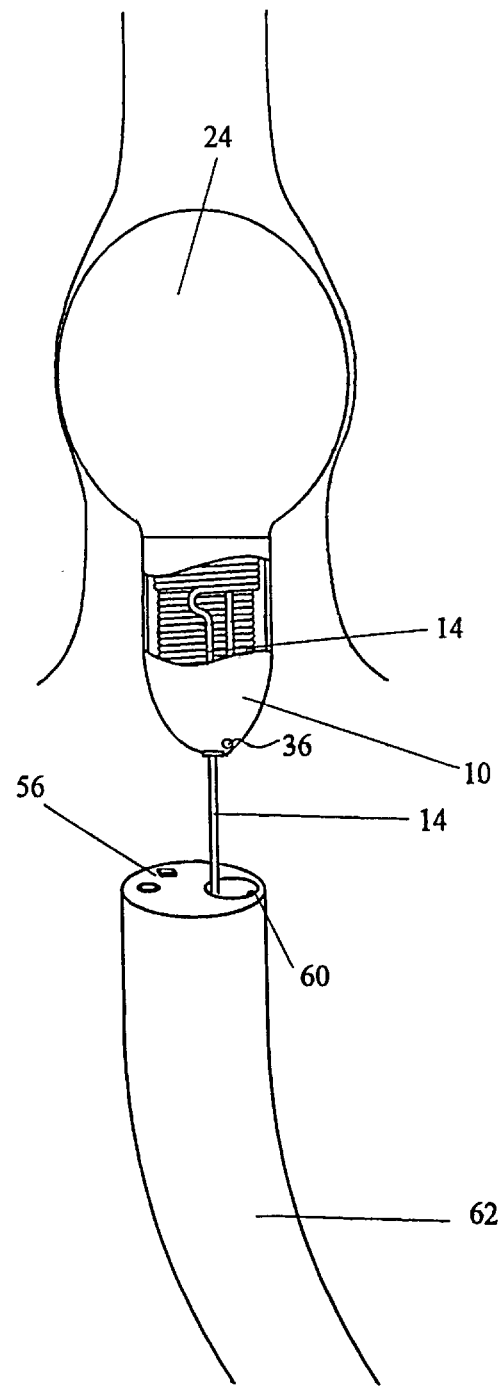
FIG.9
FIG.10

PASS-THROUGH DUODENAL ENTEROSCOPIC DEVICE

BACKGROUND OF THE INVENTION

The field of the invention pertains to devices that visualize the gastrointestinal (GI) tract from within the tract, in particular, devices such as endoscopes and enteroscopes.

Endoscopic technology has long since matured to visualize the entire colonic mucosa via colonoscopy and to visualize the esophagus, stomach and first 20 cm of the small intestine(duodenum). There is as of yet no fully satisfactory way of visualizing the full length of the small intestine. Currently, there are two types of endoscopes used to visualize the small intestine, the push endoscope and the Sonde (pull type) enteroscope. These two devices are very limited in their usefulness. The most efficacious way of inspecting the entire small bowel mucosa is to perform an intraoperative enteroscopy where the surgeon performs a laparotomy on the patient and actually moves the small intestine over the enteroscope. The enteroscope is driven by a gastroenterologist. Such a procedure is fully invasive and obviously an expensive and extreme measure to inspect the intestinal mucosa.

Adequate and efficacious visualization of the small intestine is the final frontier in the field of gastroenterology. Since the invention of the fiberoptic endoscope, there has been ceaseless improvement of upper (gastric) endoscopy and colonoscopy. Continual improvement has made inspection of the upper gastrointestinal mucosa (esophagus, stomach, and upper duodenal) a routine procedure that is highly effective and safe. Technology is now tending to plateau. For example, the current Olympus video endoscope has a scope diameter of 8 mm, and provides a high resolution magnified view of the stomach.

Similarly, colonoscopes are now highly maneuverable and quite small in diameter. Apparently it is no longer the goal of manufacturers to make smaller colonoscopes because it is believed that smaller, more flexible scopes will be more difficult to advance through the colon to the cecum.

Visualization of the small intestine, in contrast, has progressed little over the last ten years. Visualization of the small intestine is important especially in patients who have occult GI blood loss with no obvious source from the esophagus, stomach or colon. It is also important to examine the small intestine in patients with abdominal pain of unexplained origin and in patients with known diseases such as Crohn's disease or carcinoid syndrome. Barium small bowel follow-through is used most often to examine the small intestine, because of its ease and cost. However, this procedure rarely produces sufficient information for diagnoses. Physicians would usually prefer to visually inspect the small intestine mucosa if an adequate technique was available.

When a physician wishes to pursue investigation of the small intestine, the physician is left with the options of push enteroscopy, Sonde (pull type) enteroscopy or open intraoperative enteroscopy. Each of these technologies has failed to achieve widespread use because of the inherent drawbacks in each procedure.

The push enteroscope is similar in length and maneuverability to a colonoscope. However, trying to push a scope beyond the Ligament of Treitz is quite difficult because of the multiple turns of the small bowel. At best most push enteroscopes can visualize less than half of the small intestine.

The Sonde enteroscope is a narrow device about 300 cm long. The Sonde device is inserted into the stomach and then is allowed to advance through the small intestine by peristalsis. Approximately six hours are required to pass this scope through the entire length of the small intestine because of the resistance to movement. The device allows visualization of the entire small intestine when successfully passed, however, the great length of time for the procedure is a definite drawback.

The intraoperative enteroscope procedure is done when a diagnosis of small bowel pathology is sought and less invasive tests have been non-diagnostic. The procedure requires a laparotomy by a surgeon in combination with small bowel enteroscopic viewing by a gastroenterologist working in concert to advance the scope over the entire length of the small intestine. It is obviously much more risky to the patient and involves high costs and intensive use of resources.

A variety of experimental devices have been studied. These devices fall into two broad categories. The first group comprise electromechanical devices that are bendable or articulated over their length and are advanced by force produced at their proximal ends outside of the patient. The second group comprise devices that crawl by means of traction producing apparatus acting against the wall of the small intestine. The traction devices may exacerbate the potential damage to the wall of the small intestine beyond the potential damage of existing commercial enteroscopes.

Because of the failure to develop adequate means of evaluating the small intestine, patients frequently undergo a step-wise approach of undergoing one procedure followed by another, each with increasing invasiveness, risks and costs. If a device could be developed that would easily, efficiently and effectively visualize the entire length of the small intestine, this would be a dramatic step forward in the practice of medicine. To overcome the shortfalls of the existing enteroscopes and eliminate the difficulties of the crawling mechanisms, a new mechanism which enables a device to be easily delivered through the small intestine and allow access of light and power to the distal end is disclosed below.

SUMMARY OF THE INVENTION

The new pass-through duodenal enteroscopic device does not rely upon external forcing of the device or a traction mechanism on the device. Instead the natural contraction wave of the small intestine moves the device in the same manner as any other object of similar size in the small intestine. The exterior of the device is streamlined over the greater portion thereof, generally resembling an ellipsoid with the forward end slightly truncated. A flexible cord or cable extends from the device to the exterior to provide continuous communication with the device. The cable is wound inside the device and unreels as the device moves through the small intestine.

The device contains a lighting source and a charge coupled device (CCD) video camera for the purpose of visually observing the small intestine interior. Transparent inflatable means cover the camera and light to slightly expand the intestine ahead of the camera.

The cable includes electrical conduits to provide power for the light and camera and to transmit the CCD signals back to an imaging system outside the patient for the physician or technician to observe in real time. The cable may also include a fluid conduit for air or water to the device or a vacuum for sucking waste from the small intestine.

The cable comprises one or two lumen tubing about 1.5 mm in diameter. One lumen carries multiple electrical conduits in the form of very fine insulated wires. The other optional lumen comprises the fluid channel. In a preferred design, the cable automatically releases from the device when the end of the small intestine is reached. Because of the small diameter of the cable and smooth surface, the cable can be withdrawn through the esophagus. The device, detached from the cable, passes through the large intestine and from the patient.

BRIEF DESCRIPTION OF THE DRAWINGS

FIG. 9 illustrates release of the scope from the guiding tube;

FIG. 10 illustrates the scope beginning movement through the small intestine;

DESCRIPTION OF THE PREFERRED EMBODIMENT

Figure 1:
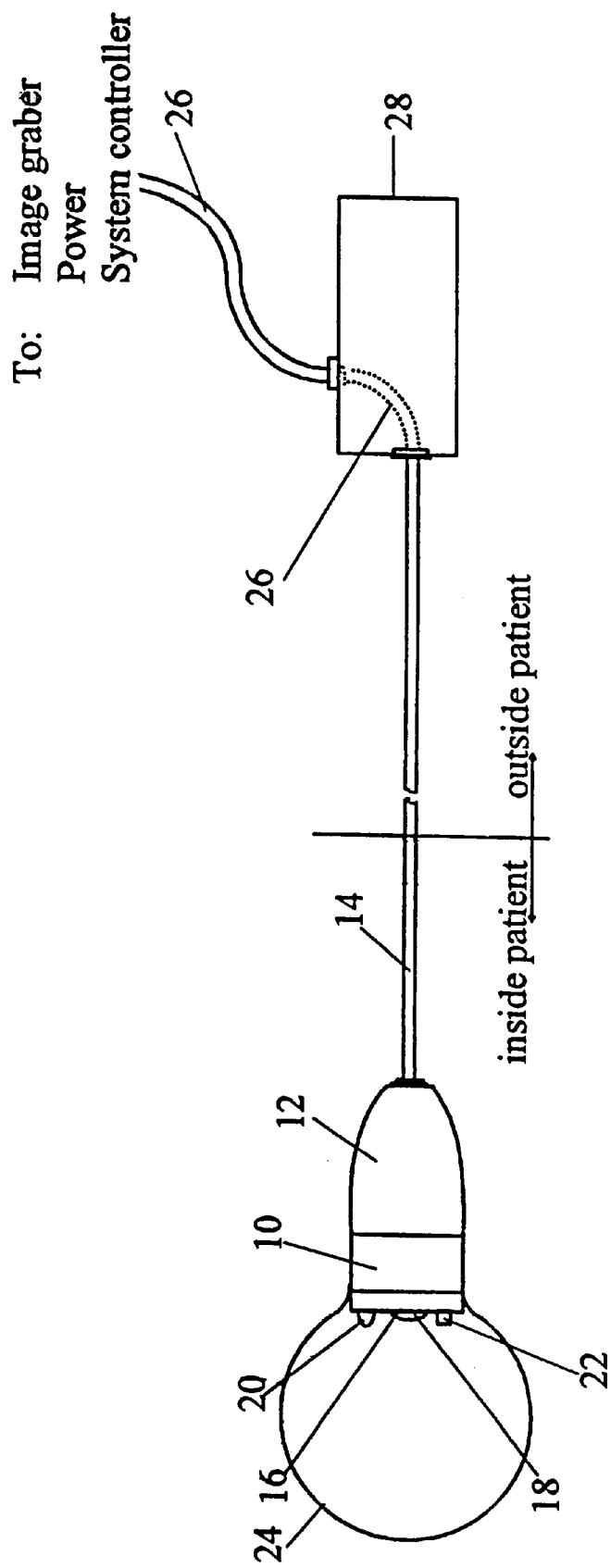
FIG. 1 is a schematic illustration of the basic components of the new pass-through enteroscope.

In FIG. 1 the new enteroscope comprises a generally ellipsoidal body 10 with a cover 12 over the rear portion and a communication cord or cable 14 extending from the rear portion. The front part of the ellipsoidal body is truncated at 16 and ported for a charge coupled device(CCD) video camera 18, a light source 20 and a fluid channel 22 for air or suction. The truncated front 16 is covered by a transparent inflatable balloon 24.

The cable 14 leads from inside the patient, through the mouth to outside the patient culminating with attachment to an electric cable 26 within a control box 28. The electric cable 26 leads to the necessary energy supply for the light source 20 and CCD camera 18 and the receiving apparatus such as an image grabber, system controller and viewing means (not shown).

The cable 14 comprises a lumen for electric communication and power wires. The cable 14 could be provided with a separate lumen for air, water or suction. However, since the cable 14 is spooled on the scope, the external diameter is constrained to limit the bulk of the cable 14 as wound on the scope and further described below. The cable 14 can be made to an outer diameter of about 1.0 mm. This overall cable 14 diameter allows about two to three meters of cable length to be compactly spooled in the scope body 10.

Figure 2:
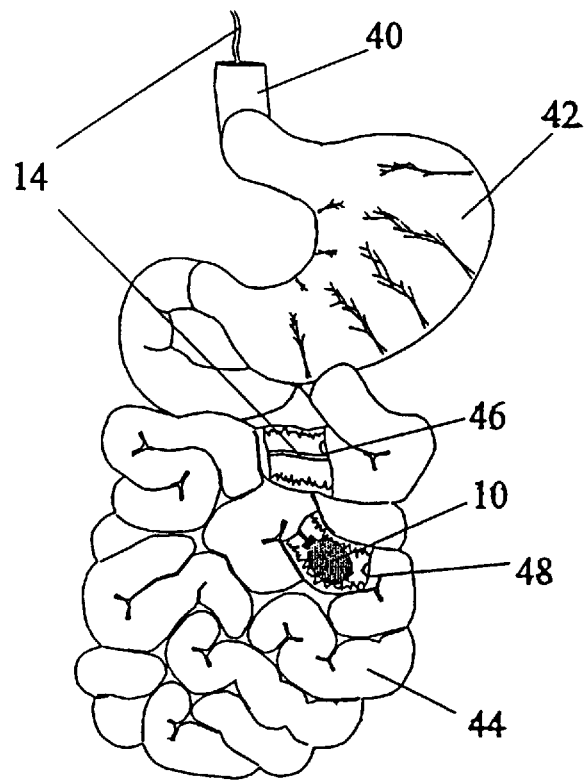
FIG. 2 is a schematic illustration of the scope and cable moving through the esophagus, stomach and small intestine.

FIG. 2 illustrates the esophagus 40, stomach 42 and very convoluted small intestine 44. The cable 14 is shown entering the esophagus 40 and traversing the small intestine 44 as shown in the cutaway portion 46. Further along the small intestine 44 a second cutaway portion 48 reveals the scope 10 as it traverses the small intestine. The driving force moving the scope 10 through the small intestine 44 is the natural motility of the small intestine. The cable 14 unspools from the scope 10 as it moves through the small intestine 44, Thus no external push or mechanical crawling force is required to move the scope 10 through the small intestine.

Figure 3:
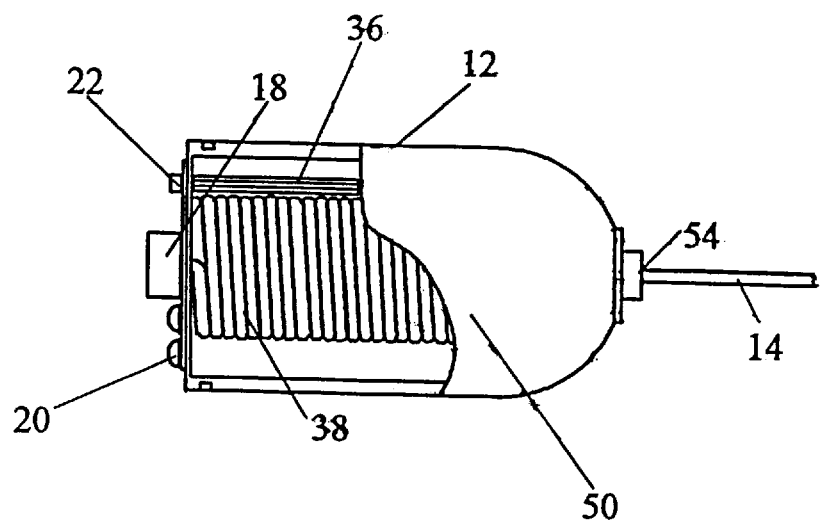
FIG. 3 schematically illustrates the principal components of the scope in partial cutaway of the housing.

As shown above in FIG. 3 the scope 10 includes a miniature color CCD camera 18 about 5–8 mm in diameter and available from Elmo ITV Div. The overall diameter of the scope 10 is about is about 25 mm in diameter thereby allowing for one or more miniature lamps 20 such as lamps from Chicago Miniature Brand Lamps, Inc. The cable 14 is spooled 50 in the scope 10 under the cover 12 and exits 54 the rear along or substantially near the scope longitudinal axis.

Figure 4:
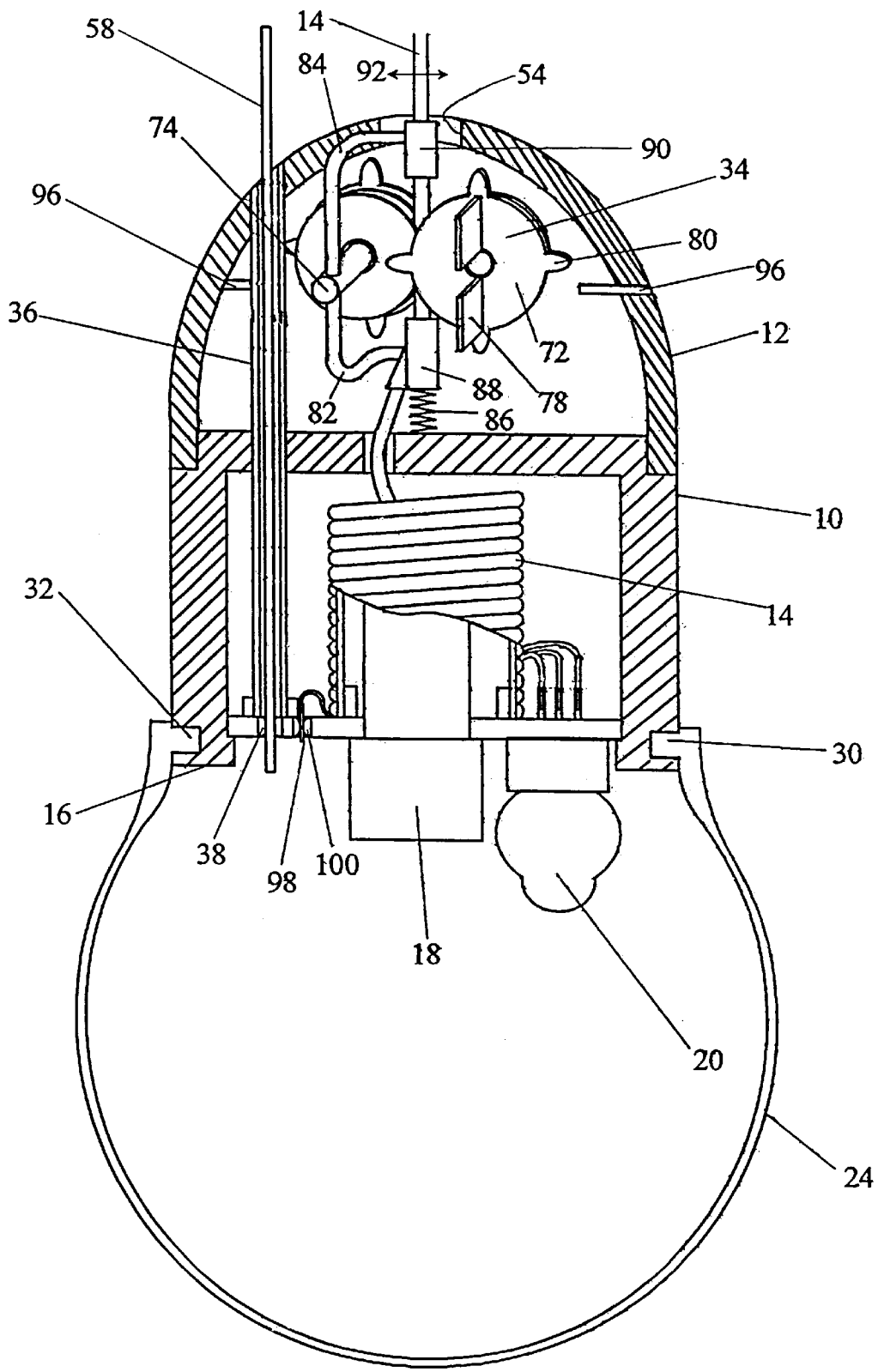
FIG. 4 is a greatly enlarged longitudinal cross-section view of the scope.

In FIG. 4 the scope body 10 has an inflatable transparent balloon or membrane 24 shown here inflated to spread out or "flatten" intestinal folds just forward of the video camera 18. The balloon 24 is molded with an elastic ring portion 30 to sealingly fit a circumferential groove 32 in the body 10. The cover 12 fits over a reorienting mechanism 34 through which the cable 14 passes. The cable 14 then passes through a rear aperture 54. In the embodiment shown in FIG. 4 the cable 14 is shown reeled on the exterior of the camera 18, however, a relatively larger reel can be configured into the scope as illustrated at 50 in FIG. 3.

Figures 5A, 5B, 5C:
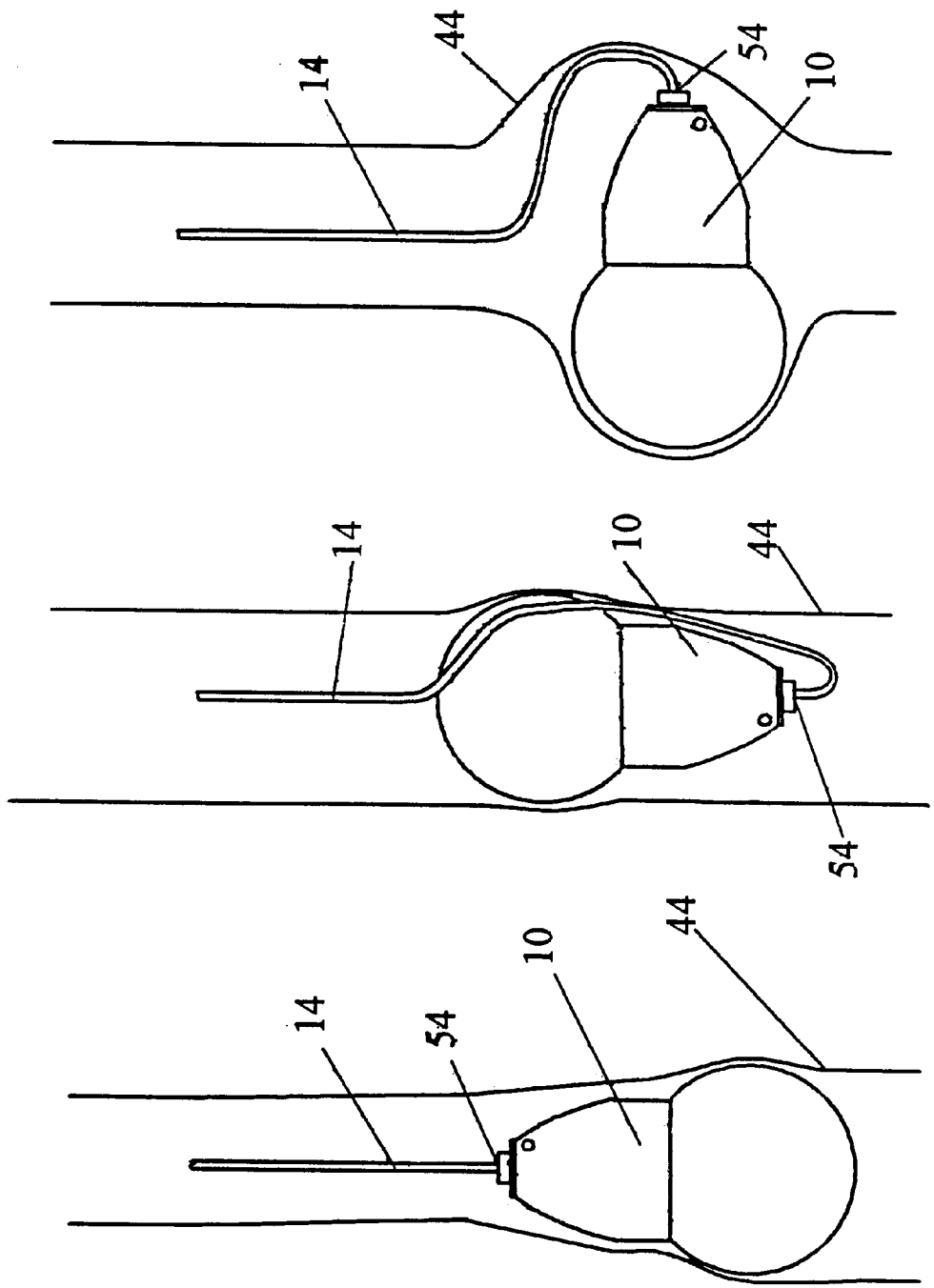
FIGS. 5a, 5b and 5c illustrate possible orientations of the scope as it traverses the small intestine.
Figure 6:
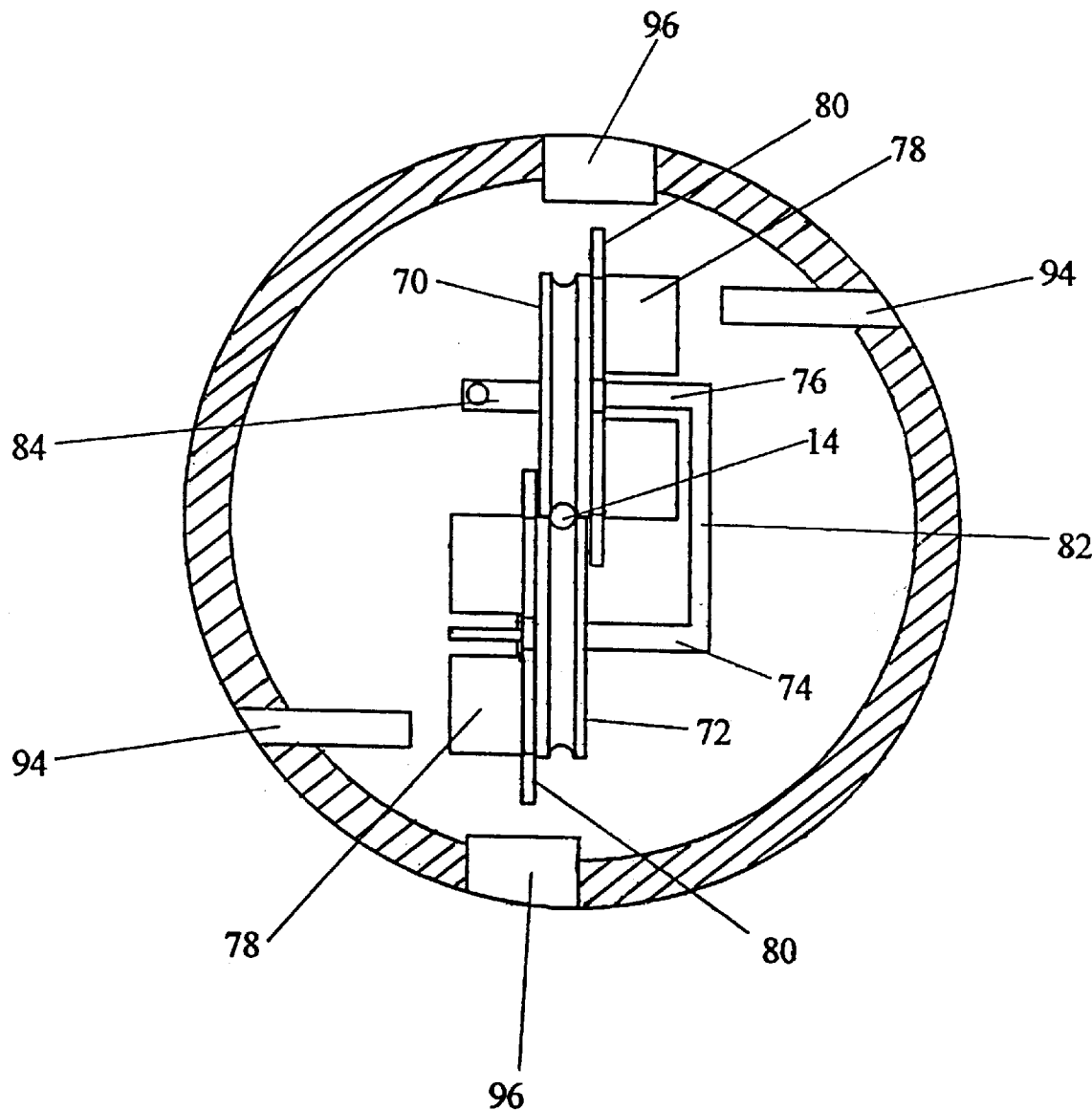
FIG. 6 is a greatly enlarged lateral cross-section view of the reorienting mechanism for the scope.

FIG. 5a illustrates the normal orientation of the scope 10 as it traverses the small intestine 44. However, in the event the scope 10 rotates out of proper orientation into a position such as shown in FIGS. 5b and 5c, a way of properly reorientating the scope 10 is required. There exists some drag force on the cable 14 as the scope 10 is drawn through the small intestine 44 by the intestinal motility. The out-of-position scope orientations of FIGS. 5b and 5c create a rotating force or couple on the scope 10 and this couple is used to trigger a reorienting mechanism 34 as shown in FIG. 4 and FIG. 6 to prevent release or unspooling of the cable 14 until the coupling force rotates the scope 10 into the proper orientation shown in FIG. 5a. With the disappearance of the coupling force the reorienting mechanism 34 releases the cable 14 to resume unspooling.

In FIGS. 4 and 6 the reorienting mechanism 34 comprises a pair of pulleys 70 and 72 between which the cable 14 passes with sufficient engagement to cause the pulleys to rotate on parallel axes 74 and 76. Each of the pulleys 70 and 72 has one or more lateral fins 78 and radial fins 80. The parallel axes 74 and 76 are provided by a framework 82 and 84. The framework 82 and 84 is supported by a spring 86 fastened to the scope body 10. The framework 82 and 84 includes a pair of guides 88 and 90 through which the cable 14 passes.

In the event the scope 10 becomes misoriented as in FIG. 5b or FIG. 5c the cable 14 is forced off-axis as indicated by arrow 92 and the reorienting mechanism 34 is also forced off-center with the result that either a lateral pulley fin 78 engages a stop 94 or a radial fin 80 engages a stop 96.

Rotation of the pulleys 70 and 72 is halted and movement of the cable 14 is halted. As a consequence the natural contraction wave of the small intestine applies a coupling force to the scope 10 to rotate the scope back into the orientation shown in FIG. 5a.

Figure 7:
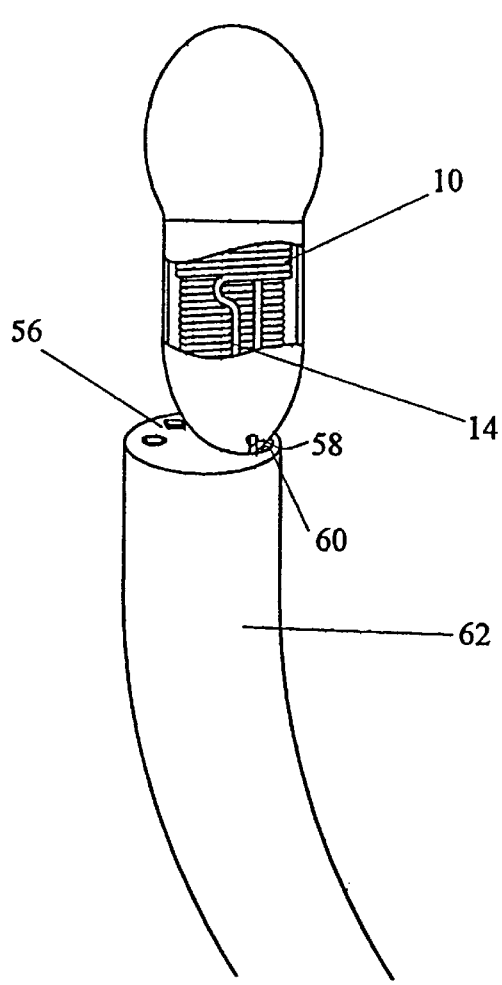
FIG. 7 schematically illustrates the scope affixed to a transesophageal guiding tube or upper GI endoscope.
Figure 8:
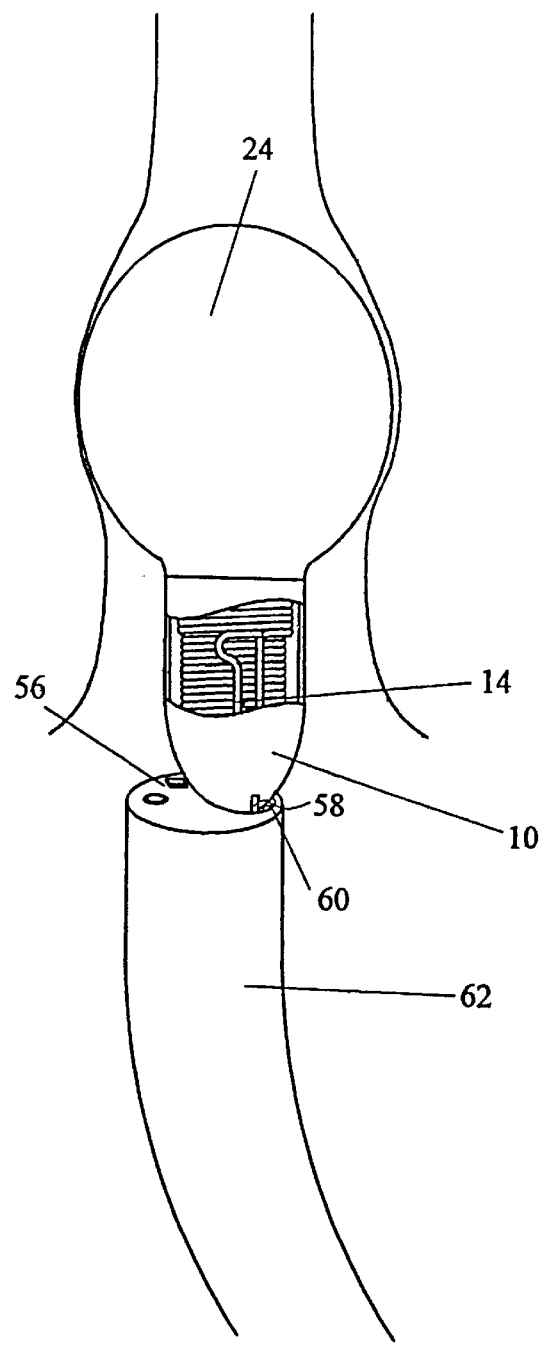
FIG. 8 illustrates the insufflation balloon expanded.

FIG. 7 illustrates the apparatus for positioning the scope 10 at the pylorus. The scope 10 is positioned at the distal end 56 of a conventional upper GI endoscope 62. In addition to the cable 14 a tubular release cable 58 passes through the biopsy channel 60 of the endoscope 62. Thus, the scope 10, attached to the endoscope 62, can be inserted into a patients' stomach in a conventional manner and then by viewing the stomach with either or both the endoscope 62 and scope 10 the scope can be inserted into the pylorus. Upon insertion the balloon 24 can be inflated as shown in FIG. 8 to open and stretch out interior folds of the small intestine and thereby to give a clear view of the intestinal surface. The tubular release cable 58 extends through an inflation tube 36 and valve 38 into the balloon 24 to provide a fluid conduit for inflation air as best shown in FIG. 4.

Figure 11:
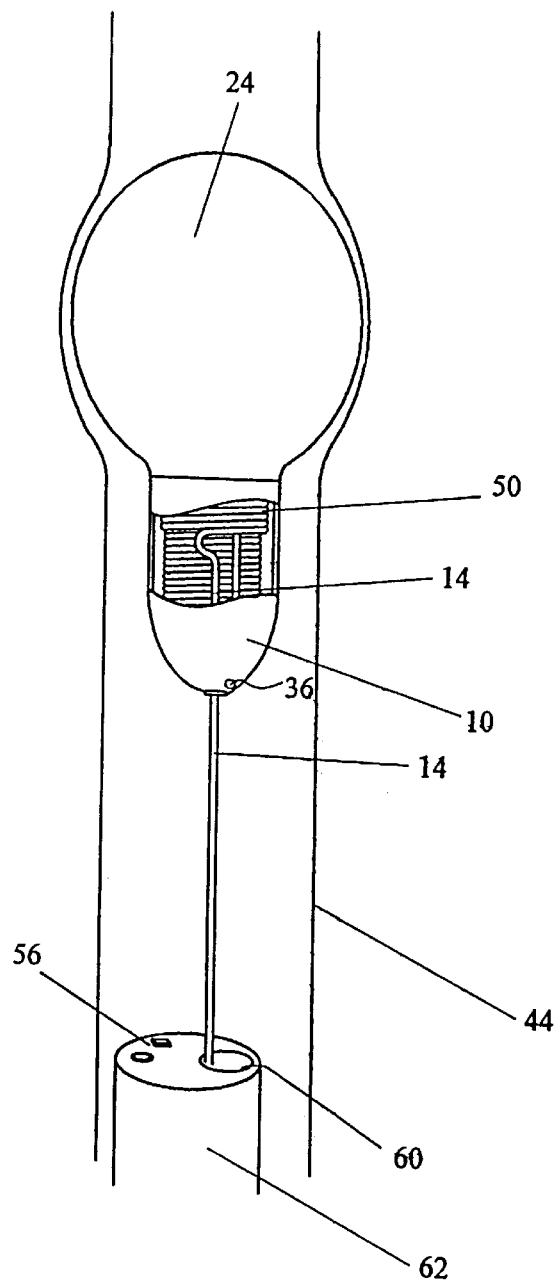
FIG. 11 illustrates the guiding tube backing off as the scope moves through the small intestine.
Figure 12:
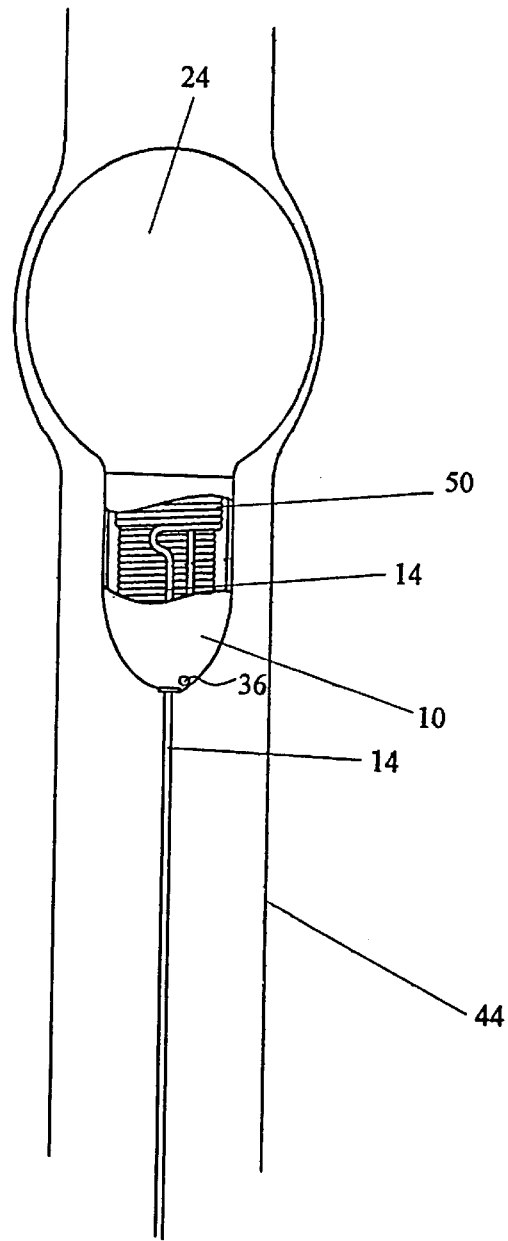
FIG. 12 illustrates the scope moving through the small intestine as it temporarily expands the passageway.

In FIG. 9 the release cable 58 is retracted from the inflation tube 36 and as shown in FIG. 10 the scope 10 begins to traverse the small intestine with the balloon 24 stretching the small intestine for a clear view in front of the scope. Release of the scope 10 is effected by retracting the release cable 58 from the valve 38 and inflation tube 36 thus sealing the inflated balloon 24. In FIG. 11 the scope 10 traverses the small intestine 44 and in FIG. 12 the scope traverses regions of the small intestine of a diameter somewhat smaller than the diameter of the scope.

Figure 13C:
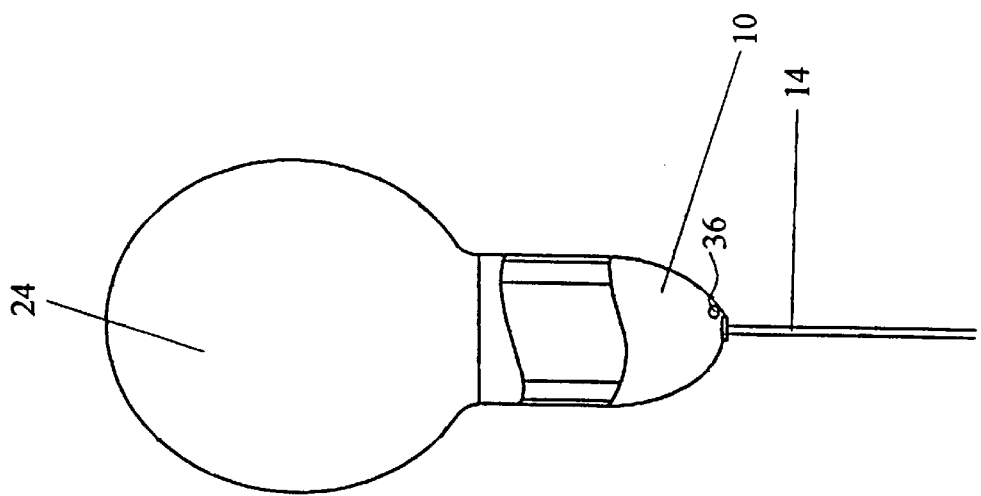
FIGS. 13a, 13b and 13c illustrate in detail the uncoiling of the cable from the scope during traverse of the small intestine.
Figure 13B:
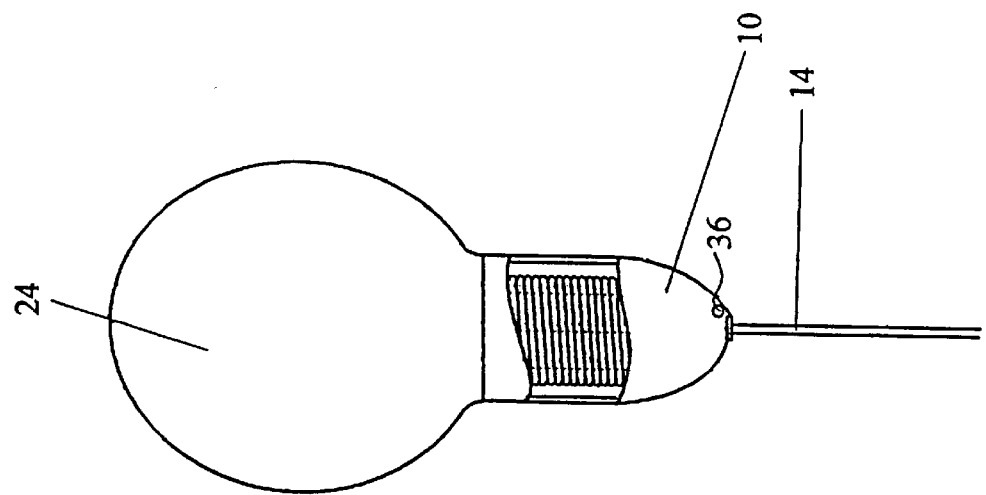
Figure 13A:
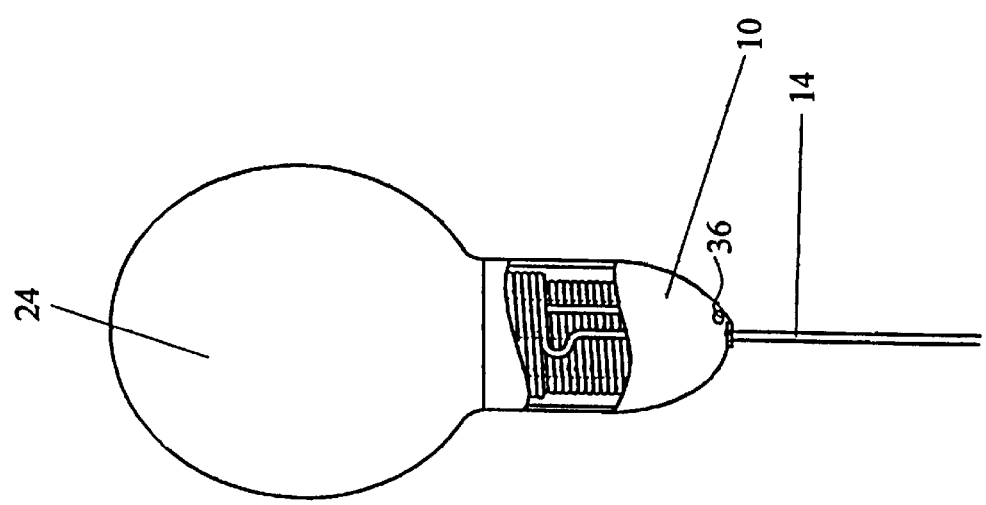

When the scope 10 reaches the terminal ileum the cable 14 is caused to release from the scope 10 and the balloon 24 deflated. The release can be essentially automatic as illustrated in FIGS. 13a, 13b and 13c and 14. The cable 14 unreels from inside the scope 10 as shown in FIGS. 13a and 13b. Upon fully unreeling the cable 14 pulls a pin 98 from a second valve 100 adjacent the valve 38. The end of cable 14 is connected to the pin 98 by a pigtail 102 to a connector 104 that also connects the power and communication wires to the scope 10. With the pin pulled from valve 100, valve 100 does not fully close, but rather remains partially open to allow the balloon 24 to deflate.

Figure 15:
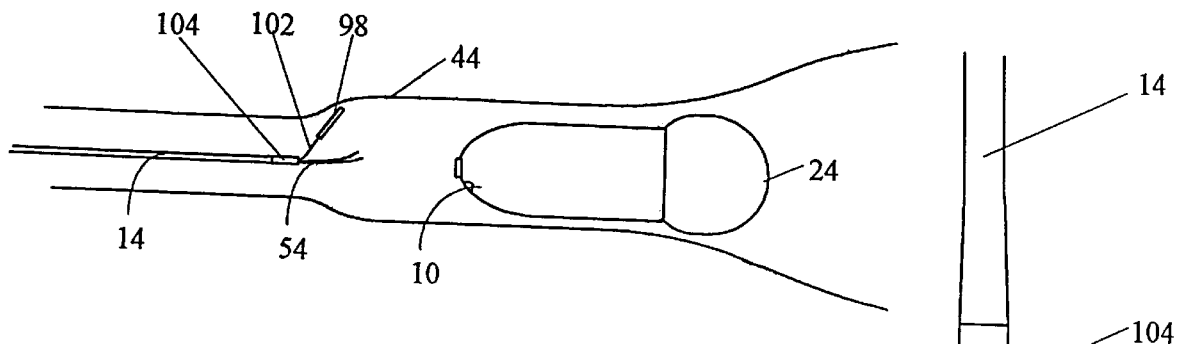
FIG. 15 schematically illustrates release of the cable upon traversal of the small intestine and deflation of the balloon cover.
Figure 14:
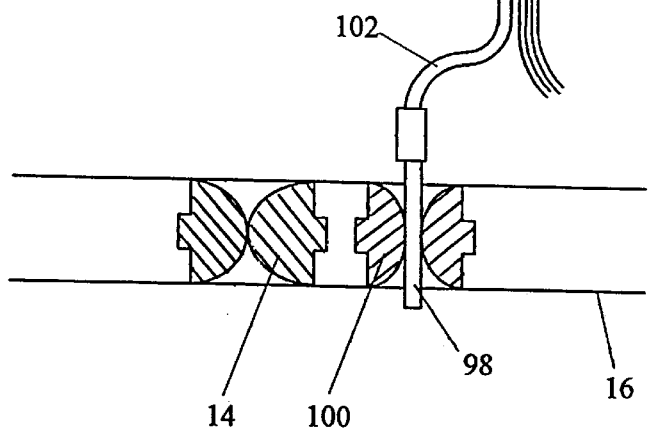
FIG. 14 details the sealing valves for the inflatable balloon cover.

As the cable 14 exits the scope 10 as shown in FIG. 15 the pin 98 and pigtail 102 remain attached but the power and communication wires have been released from the connector 104. As an alternative to the connector 104, the power and communication wires may be provided with a break point that fractures with the application of tension upon full unreeling of the cable 14.

The cable 14, being very small in diameter, can be retracted through the mouth of the patient. The scope 10 passes on through the large intestine and rectum from the patient.

I claim:

1. An enteroscope comprising a generally oblong body having a viewing end and a tail end, said viewing end having camera means and illumination means adapted to view and illuminate a small intestine interior,
    a cable storable in the body and adapted to unreel as the body moves through the small intestine, said cable enclosing electrical means connected to the body, and
    said body sized and shaped for movement through the small intestine in response to the natural wave of the small intestine in moving objects therethrough.

2. The enteroscope of claim 1 including an inflatable transparent membrane covering at least a portion of the viewing end of the body.

3. The enteroscope of claim 2 including means on the body to inflate and deflate the membrane.

4. The enteroscope of claim 2 including tubular means connectable to the body to inflate the membrane.

5. The enteroscope of claim 4 wherein the tubular means is adapted to release the body for movement through the small intestine.

6. The enteroscope of claim 2 wherein the camera means is covered by the membrane and adapted to gather light transmitted through the membrane.

7. The enteroscope of claim 6 wherein the illumination means is covered by the membrane and adapted to transmit light through the membrane.

8. The enteroscope of claim 1 including automatic coupling means engageable to prevent unreeling of the cable in response to misalignment of the body in the small intestine.

9. The enteroscope of claim 2 including automatic termination means adapted to cause deflation of the membrane.

10. The enteroscope of claim 1 including automatic termination means adapted to detach the cable upon completion of viewing of the small intestine.

11. The method of inspecting the interior of the small intestine comprising the steps of:
    placing a body having a video camera and illumination means therein at the entrance to the small intestine,
    allowing the entire body to be propelled through the small intestine in response to the natural contraction wave of the small intestine,
    viewing the interior of the small intestine as the entire body proceeds through the small intestine in response to the natural contraction wave of the small intestine and
    terminating viewing by the video camera and allowing the body to pass into and through the large intestine.

12. The method of claim 11 wherein viewing of the small intestine proceeds through the entire length of the small intestine.

13. The method of claim 12 wherein viewing is terminated by automatic means on the body.

14. The method of claim 11 wherein misalignment events occurring during movement of the body through the small intestine are corrected by automatic coupling means engaged in response to the misalignment.

15. The method of claim 11 including temporary expansion of the interior region of the small intestine viewable by the video camera.

16. The method of claim 15 wherein the expanded interior region of the small intestine is viewed through the expansion means.

17. An enteroscope comprising a generally oblong body having a viewing end and a tail end, said viewing end having camera means and illumination means adapted to view and illuminate a small intestine interior,
    an inflatable transparent membrane covering at least a portion of the viewing end of the body,
    said body shaped and sized for movement through the small intestine in response to the natural wave of the small intestine in moving objects therethrough, and
    automatic termination means adapted to cause deflation of the membrane.

18. The enteroscope of claim 17 including means on the body to inflate and deflate the membrane.

19. The enteroscope of claim 18 wherein the camera means is covered by the membrane and adapted to gather light transmitted through the membrane.

20. The enteroscope of claim 18 wherein the illumination means is covered by the membrane and adapted to transmit light through the membrane.

21. An enteroscope comprising a generally oblong body having a viewing end and a tail end, said viewing end having camera means and illumination means adapted to view and illuminate a small intestine interior, said tail end having a cable attached thereto, said body shaped and sized for movement of the entire body including the tail end through the small intestine in response to the natural wave of the small intestine in moving objects therethrough, and automatic termination means adapted to detach the cable upon completion of viewing of the small intestine.

* * * * *